United States Patent [19]
Marr

[11] Patent Number: 5,029,485
[45] Date of Patent: Jul. 9, 1991

[54] APPARATUS AND METHOD FOR REMOTELY SAMPLING FLUID

[75] Inventor: Alexander H. Marr, Huntington Beach, Calif.

[73] Assignee: Southern California Edison, Rosemead, Calif.

[21] Appl. No.: 419,485

[22] Filed: Oct. 10, 1989

[51] Int. Cl.$^5$ .............................................. G01N 1/14
[52] U.S. Cl. .............................. 73/864.34; 73/864.31; 73/864.73
[58] Field of Search .......... 73/864.34, 864.35, 863.83, 73/863.84, 863.85, 863.86, 864.73, 864.74, 864.31, 864.32, 864.11, 864.18, 864.24, 864.25, 863.81, 863.82; 137/315, 317, 319, 327, 328

[56] References Cited

U.S. PATENT DOCUMENTS

| | | |
|---|---|---|
| 3,153,345 | 10/1964 | Berg . |
| 3,412,613 | 11/1968 | Brown et al. ..................... 73/863.85 |
| 3,576,195 | 4/1971 | Richard, Jr. ...................... 137/317 |
| 3,724,276 | 4/1973 | Schwind . |
| 3,822,597 | 7/1974 | Clark . |
| 3,829,761 | 8/1974 | Shimizu et al. ................. 137/317 X |
| 3,896,673 | 7/1975 | Audouze et al. . |
| 3,915,651 | 10/1975 | Nishi .............................. 73/864.16 |
| 3,992,155 | 11/1976 | Nilsson ........................... 137/99 X |
| 4,003,260 | 1/1977 | Catoul .......................... 73/864.31 X |
| 4,409,814 | 10/1983 | Onuma et al. ...................... 73/19 |
| 4,467,648 | 8/1984 | Sasaki ......................... 73/864.31 X |
| 4,615,515 | 10/1986 | Dancoine .................... 73/863.83 X |

FOREIGN PATENT DOCUMENTS

| | | |
|---|---|---|
| 2143045 | 3/1972 | Fed. Rep. of Germany ... 73/863.83 |
| 2101234 | 8/1972 | Fed. Rep. of Germany ... 73/864.34 |
| 146855 | 3/1981 | German Democratic Rep. .................................. 73/864.73 |
| 60-123749 | 7/1985 | Japan .............................. 73/864.73 |
| 60-135836 | 7/1985 | Japan .............................. 73/864.73 |
| 1346962 | 10/1987 | U.S.S.R. ......................... 73/864.73 |

*Primary Examiner*—Tom Noland
*Attorney, Agent, or Firm*—Denton L. Anderson; Sheldon & Mak

[57] ABSTRACT

A fluid sampling apparatus and method for remotely sampling insulating fluid in a high voltage, high amperage electrical switch without de-energizing the switch. The apparatus includes a sampling tube, a supporting structure for the tube, a rack and pinion gear assembly for lowering and raising the tube, and an elongated handle for operating the gear assembly. The fluid sample is collected in a sample bottle fluidly connected to an overflow bottle and a vacuum pump for withdrawing the insulating fluid. The sampling tool is made mostly of electrically insulating plastic. A removing tool for remotely removing a plug from the electrical switch is used. The removing tool comprises a socket, a socket extender, a ratchet wrench attachable to the extender, and two pull cords for remotely operating the wrench.

33 Claims, 3 Drawing Sheets

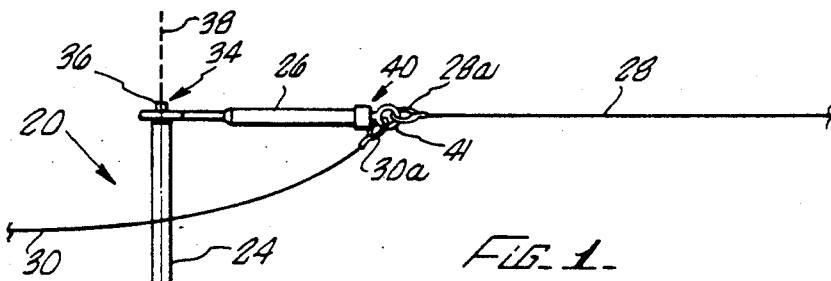
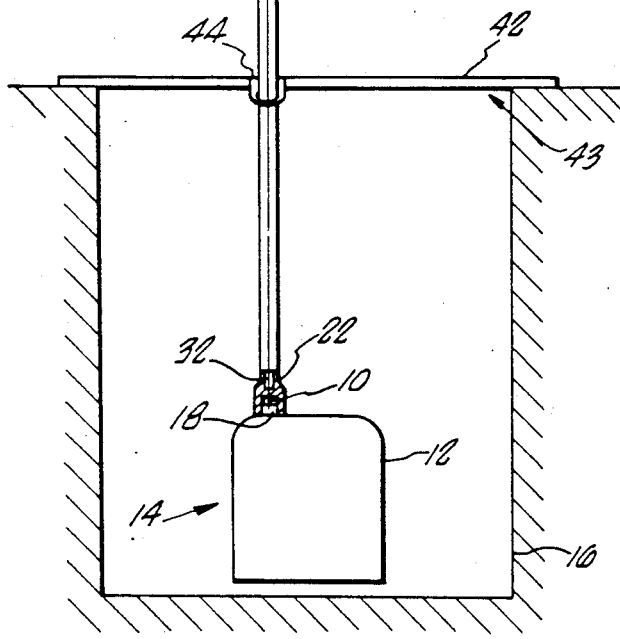
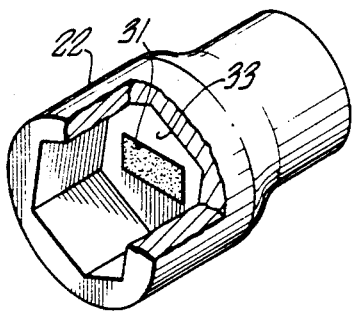
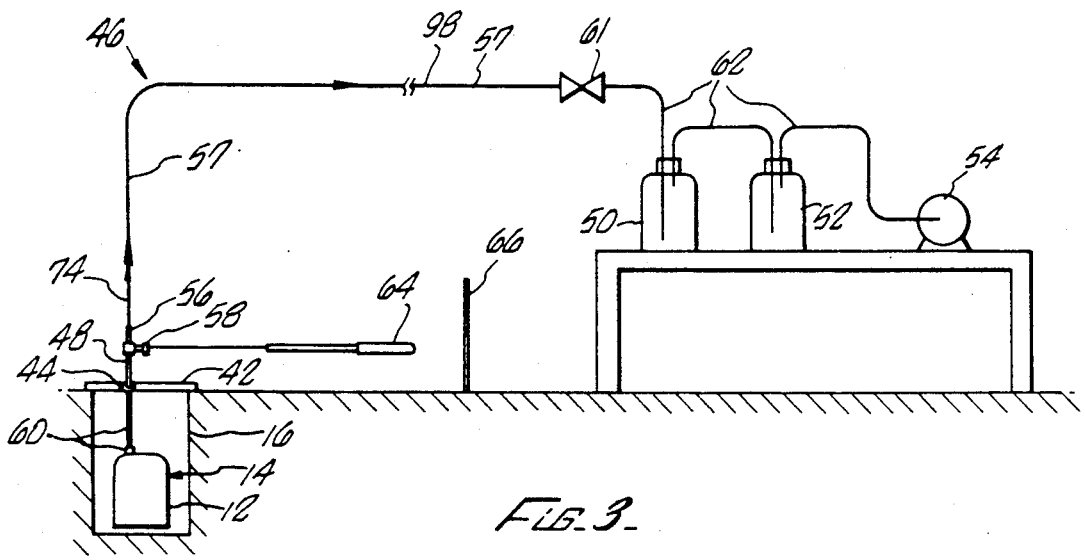

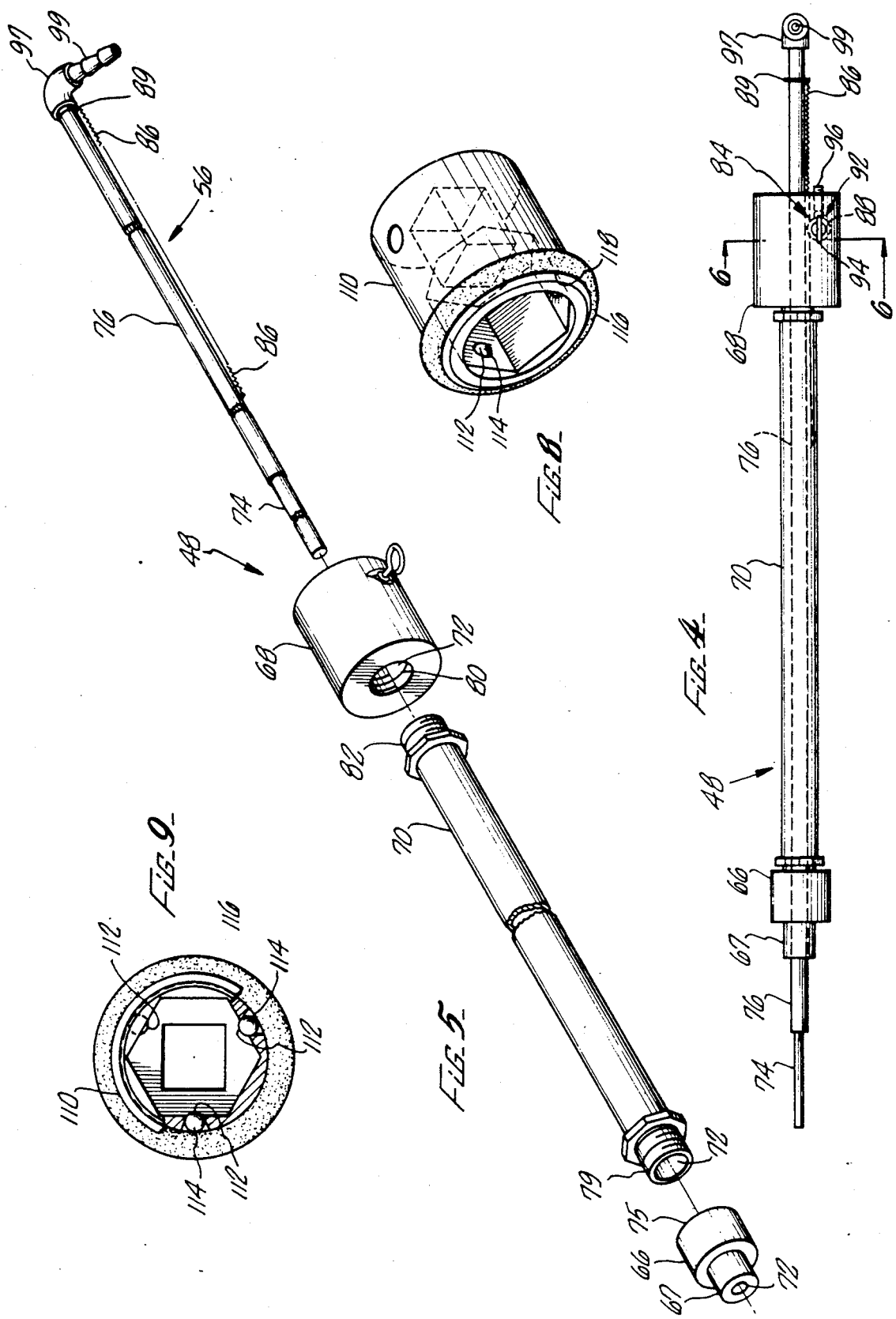

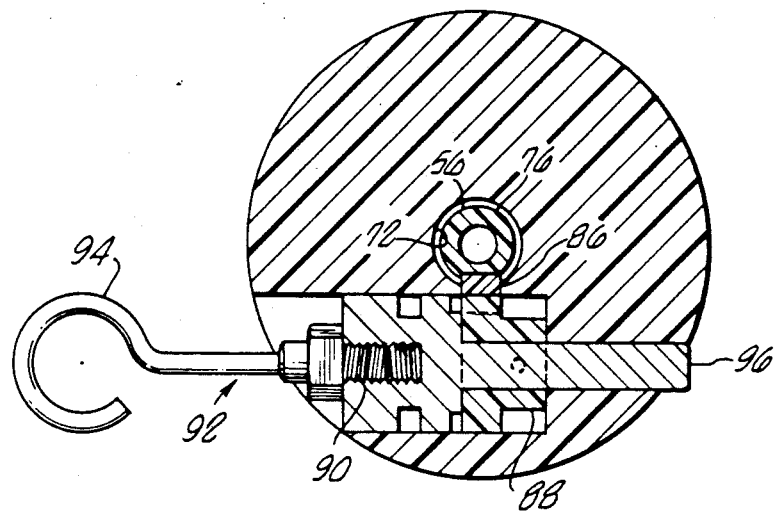
Fig_6_
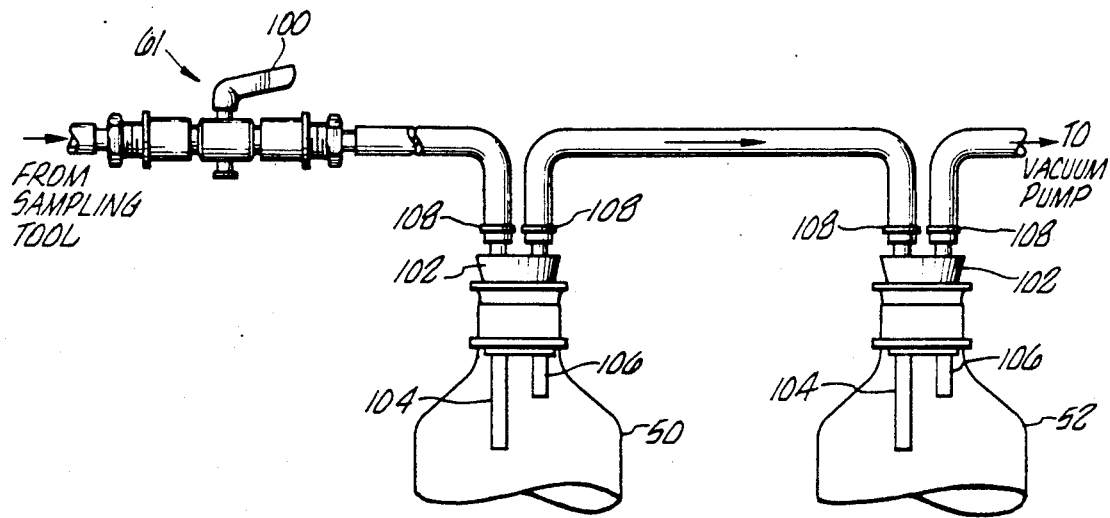
Fig_7_

APPARATUS AND METHOD FOR REMOTELY SAMPLING FLUID

BACKGROUND

The present invention relates to the sampling of fluid in a fluid reservoir. More specifically, the present invention concerns devices and methods for sampling fluid remotely and with minimal disturbance of the fluid.

It is often desirable to remotely withdraw fluid samples from a reservoir, while minimizing the disturbance of the fluid in the reservoir during sampling. For example, such sampling is desirable when a fluid sample is taken from the reservoir of a high voltage, high amperage switch in an electrical power distribution system.

Insulating liquid (which is usually a petroleum-based oil) is often provided in a high voltage, high amperage electrical switch to extinguish the electrical arc which is otherwise produced when the switch is de-energized. The insulating quality of the liquid in these switches has a direct bearing on their reliability and operation. The liquid can lose insulating quality through contamination with non-insulating material, frequency of use, or the mere passage of time. In particular, the insulating quality of the liquid can be reduced when metal components or gaskets in the switch corrode thereby allowing metal particles and/or water to get into the liquid.

Failing to replace degraded insulating liquid in an electrical switch, or to replace the entire switch, can result in switch failure. In a utility power distribution system, a switch failure can in turn cause substantial system maintenance costs, lost revenues, and dissatisfied utility customers. Therefore, the liquid in these electrical switches should be periodically checked to determine whether the insulating liquid or the switch ought to be replaced.

The conventional way of checking the quality of the insulating liquid is to first de-energize the switch. Next, a plug from the reservoir containing the insulating liquid is removed and a sample of the insulating liquid is taken. The sample is then tested for its insulating characteristics.

The foregoing procedure has substantial drawbacks because, before the switch can be de-energized, it must be isolated within the electric power system to avoid interrupting service. Power system switch isolation requires complex and expensive measures, including substantial manpower. As a result, sampling of the insulating liquid in such switches is infrequent. The switches are generally sampled only when visual inspection reveals evidence of potential breakdown of insulating liquid, such as corrosion on the outside surfaces of a switch. However, breakdown of the insulating liquid can occur without such external evidence of corrosion. Consequently, more switch failures take place than would otherwise occur if the insulating liquid could be tested without de-energizing the switch.

There is therefore a need for a device and method for remotely sampling insulating fluid in an electrical switch without de-energizing the switch. Stated another way, there is a need for a device and method for remotely removing a plug on a fluid reservoir of an electrical switch and for remotely sampling the fluid without substantially disturbing the fluid.

SUMMARY

The present invention meets the foregoing needs. The present invention is directed to a fluid sampling apparatus, kit, and method for remotely sampling an insulating fluid in an arc-extinguishing reservoir of a high voltage, high amperage electrical switch without de-energizing the switch. The sampling apparatus includes a sampling tube, an actuator for inserting the tube into the reservoir and removing the tube from the reservoir, a support for supporting the tube near the reservoir, collection means in fluid communication with the tube for collecting a fluid sample, and means for fluidly connecting the tube to a pumping means for withdrawing a sample of the fluid through the tube into the collection means. The actuator is operable at a distance of at least about ten feet from the reservoir and is electrically insulated from the switch to avoid electrical shock to an operator of the tool.

The actuator can comprise a rack and pinion gear assembly attached to the tube and an elongated handle for remotely and manually operating the gear assembly to insert the tube into and remove the tube from the reservoir. The actuator can lower and raise the tube without rotating it to minimize disturbance of the fluid in the reservoir.

A kit according to the present invention comprises the sampling apparatus and a removing tool for removing a plug from the opening of the reservoir. The removing tool can comprise a socket to fit the plug, a socket extender attachable to the socket, a ratchet wrench attachable to the extender, and pull cords, attachable to the wrench, for rotating the wrench to remove the plug from or replace the plug on the reservoir.

DRAWINGS

These and other features, aspects, and advantages of the present invention will become better understood with reference to the following description, appended claims, and accompanying drawings, where:

FIG. 1 is a schematic view of a removing tool according to the present invention being used to remove a threaded plug from a Burd electrical switch;

FIG. 2 is a partial cross-sectional view of a socket as used in the removing tool of FIG. 1;

FIG. 3 schematically illustrates a fluid sampling apparatus according to the present invention for sampling the fluid in the reservoir of a Burd electrical switch;

FIG. 4 is an assembled view of a portion of a fluid sampling tool according to the present invention;

FIG. 5 is an exploded view of the portion of the fluid sampling tool of FIG. 4;

FIG. 6 is a cross-sectional top view of the rack and pinion gear assembly and assembly housing of the sampling tool taken along line 6—6 of FIG. 4;

FIG. 7 is a side view of the connections between the fluid sampling tool, the vacuum bottles, and the vacuum pump which are schematically illustrated in FIG. 3;

FIG. 8 is a perspective view of a gripping socket as used in the removing tool of FIG. 1; and FIG. 9 is a bottom view of the socket of FIG. 8.

DESCRIPTION

Turning to the drawings, FIG. 1 illustrates a removing tool 20 according to the present invention which can be used to remove a threaded level sight gauge or plug 10 from a reservoir 12 of a Burd electrical switch 14 located in an underground vault 16 of a utility power system. The Burd electrical switch is typically a 12 to 16 kV/600 amp switch, but can be of higher or lower voltage and/or amperage. After the plug 10 is removed, a sample of insulating fluid can be withdrawn through an opening 18 of the reservoir 12 and tested for its insulating qualities.

The removing tool 20 comprises a socket 22 which fits the plug 10, an elongated socket extender 24, a ratchet wrench 26, and attachable pull cords 28 and 30. The socket extender 24 can be removably attachable at its socket end 32 to the socket 22 in a conventional manner, as illustrated in cross-section. When the socket extender 24 is attached to the socket 22, the extender 24 is fixed against rotation in relation to the socket 22. The ratchet wrench 26 can also be removably attachable at is first end 34 to a handle end 36 of the socket extender 24 in a conventional manner. For example, the handle end 36 can have a hexagonal cross-section which fits snugly into a matching hexagonal opening in the first end 34. As the wrench 26 is rotated in a selected non-ratcheting direction, the extender 24, the socket 22, and the plug 10 rotate in the same direction.

The ratchet wrench 26 extends at a substantially right angle from the socket extender 24 and is capable of ratcheting in relation to the socket extender 24 about a ratcheting axis 38 through the socket extender 24. The pull cords 28 and 30 are attachable to and extend from a second end 40 of the ratchet wrench 26 for rotating the ratchet wrench 26 in opposite directions of rotation about the axis 38. The cords 28 and 30 can be attached to the ratchet wrench 26 in a conventional manner. For example, a fixed ring 41 can extend from the second end 40 which can in turn be attached to cord rings 28a and 30a.

The removing tool 20 can be stabilized on the socket 22 with a cross-brace 42 extending across an opening 43 of the vault 16. The cross-brace 42 can be snugly attached to a holding clip 44 for retaining the tool 20. Before the tool 20 is used to remove the plug 10, the holding clip 44 is preferably in vertical alignment with the plug 10 and the area of the switch 14 around the plug 10 is cleaned with solvent.

As illustrated in FIG. 2, a piece of tape 31 which is sticky on both sides is attached to a back wall 33 of the socket 22. The tape 31 is for retaining the plug 10 in the socket 22 when the plug 10 is removed from the opening 18 and lifted out of the vault 16.

Prior to removing the plug 10 from the reservoir 12, the switch 14 is checked for excessive corrosion or other signs of a need for switch replacement. For example, if the top of the switch 14 is concave, the switch 14 is preferably replaced instead of sampling the fluid inside. Also, if the insulating fluid level in the switch 14 is abnormally low or the corrosion on the outside of the switch is high, the switch 14 is replaced rather than sampled.

During operation, the removing tool 20 preferably has two operators. When the plug 10 is to be removed from the switch 14, the ratchet on the wrench 26 is set to be fixed against ratcheting in a counter-clockwise direction of rotation. One operator pulls on the cord 28 to unscrew the plug 10 (which can be unscrewed in a counter-clockwise direction of rotation). The other operator then pulls on the cord 30 to ratchet the wrench 26 back to its initial position. This process is repeated until the plug is loosened from the switch 14 so it can be pulled away from the opening 18.

The removing tool 20 can be operated remotely from the reservoir 12. Preferably, an operator of the tool 20 is fifteen feet or more from the underground vault 16 when operating the removing tool 20. However, the removing tool 20 ordinarily serves its purpose if the operator is approximately a distance of ten feet or more from the reservoir 12 while operating the tool 20.

The tool 20 can also be used to replace the plug 10 on the switch 14 after a fluid sample has been withdrawn from the reservoir 12. The method of operation is essentially the same as when removing the plug 10, except the wrench 26 is set to ratchet in the opposite direction. Before replacing the plug 10, it can be advisable to provide an appropriate sealant on its threads.

Turning to FIG. 3, a fluid sampling apparatus 46 according to the present invention is schematically illustrated. The apparatus 46 comprises a fluid sampling tool 48 installed on the switch 14, a sample bottle 50 in fluid connection with the sampling tool 48, an overflow bottle 52 downstream from the sample bottle 50, and connector tubing 62 which can be connected to a vacuum pump 54 thereby providing fluid connection with the bottles 50 and 52. The fluid sampling tool 48 comprises (1) a sampling tube 56 which extends into the switch 14 through the opening 18 and is fluidly connected to flexible tubing 57 which is a portion of the tube 56, (2) an actuator 58 for remotely lowering and raising the tube 56 into and from the reservoir 12, (3) a support 60 for supporting the tool 48 near the opening 18, and (4) a valve connector assembly 61 for fluidly connecting the tool 48 to the sample bottle 50.

The portions of the tube 56 and the support 60 in contact with the switch 14 (e.g., the adapter 66 shown in FIGS. 5 and 6) or the insulating fluid in the switch 14 can be made of insulating material to provide an insulating means for the sampling tool 48. Preferably, the contact portions of the tube 56 and the adapter 66 are made of material with a high dielectric strength, such as the acetal resin thermoplastics sold under the registered trademark DELRIN (hereinafter referred to as "acetal resin"). This is because the material for these components should be non-conducting at the service voltage where the electrical switch is being sampled. Burd switches are typically at a service voltage of about 12 kV to 16 kV, but the voltage can be higher or lower depending upon the location within the electrical power system. Therefore, the required dielectric strength of the materials used may vary with the particular switch 14 being sampled. Acetal resin has sufficient dielectric strength in most, if not all, applications. As further insulative protection, the gear housing 68 shown in FIGS. 4 and 5 can also be made of acetal resin.

The vacuum pump 54 can be one driven by a 120 volt AC power source. The actuator 58 can comprise an elongated telescopic handle 64 which is rotatable to lower the tube 56 into the reservoir 12.

The flexible tubing 57 is fluidly connected to the vacuum pump 54 by connector tubing 62 between the valve connector assembly 61 and the sample bottle 50, between the bottles 50 and 52, and between the overflow bottle 52 and the pump 54. The connector tubing 62 is vacuum-sealed to the bottles 50 and 52 in a conventional manner. The vacuum-sealing apparatus is illustrated in more detail in FIG. 7, and is described below in connection therewith. The overflow bottle 52 is provided to prevent insulating fluid from sucking into the vacuum pump 54 should the sample bottle 50 be overfilled. Preferably, the bottles 50 and 52 are coated with or made of soft plastic so they are shatter-proof.

The apparatus 46 can be operated remotely from the reservoir 12. As is the case with the removing tool 20, an operator of the apparatus 46 is preferably about fifteen feet or more from the reservoir 12 when operating the apparatus 46. However, the apparatus 46 would ordinarily serve its purpose when the operator is a distance of approximately ten feet from the reservoir 12. To further protect the operator, a barrier 66 can be erected between the operator and the reservoir 12.

In preparing to operate the apparatus 46, the sampling tool 48 is vertically lowered through the retaining clip 44 of the brace 42 into the vault 16. The sampling tool 48 preferably fits snugly on the opening 18.

To manually operate the apparatus 46, the operator rotates the handle 64 to lower the tube 56 into the reservoir 12. The vacuum pump 54 is then switched on for suction pumping a fluid sample from the reservoir 12, through the tube 56, through the tubing 57 and 62, and into the sample bottle 50. Preferably, the sample bottle 50 is first filled to about half its capacity, discarded as waste after the pump 54 is temporarily turned off and the valve 100 is closed, and replaced with a new sample bottle 50 for sample collecting. The pump 54 is then reactivated and the valve 100 is opened. The foregoing procedural steps assure that a true sample of the fluid in the reservoir 12 is obtained. When the new sample bottle 50 is filled to a desired level, the pump 54 is turned off, the valve 100 is closed, and the handle 64 is rotated in a reverse direction to raise the tube 56 from the reservoir 12. The apparatus 46 can then be removed from the vault 16 and the plug 10 can be replaced on the switch 14 with the removing tool 20, as described above.

A portion of the fluid sampling tool 48 is illustrated in more detail in FIGS. 4, 5, and 6. The support 60 of the sampling tool 48 comprises an end adapter 66, a gear housing 68, and a connector housing 70 attachable between the adapter 66 and the gear housing 68. The adapter 66 and the housings 68 and 70 have receiving holes 72 for receiving the tube 56 therethrough. Preferably, the tube 56 fits snugly and slidably into the receiving holes 72 of at least the adapter 66 and the gear housing 68 to provide support for the tube 56. In the embodiment of the invention illustrated in the drawings, the receiving hole 72 of the gear housing 68 is of smallest diameter in the upper portion of the gear housing 68 to snugly fit the tube 56. The tube 56 further has a sampling end 76 with walls of lesser thickness than the rest of the tube 56 for insertion into the reservoir 12. The thinner-walled sampling end 76 minimizes disturbance of the insulating fluid in the reservoir 12 and/or better fits a withdrawal tube which is inside some switches. The lower vertical portion 74 and the sampling end 76 of the tube 56 can be of varying lengths, depending on the depth of the vault 16 and the desired sampling depth in the reservoir 12.

The adapter 66 has a first female threaded portion 78 for threadedly receiving a corresponding first male threaded protrusion 79 extending from the connector housing 70. The gear housing 68 has a second female threaded portion 80 for threadedly receiving a corresponding second male threaded protrusion 82 extending from the housing 70. The adapter 66 and the housing 68 and 70 can thereby be connected to each other for receiving the tube 56 therethrough. The connector housing 70 can be of varying lengths to appropriately fit the lengths of the upper vertical portion 74 and sampling end 76 of the tube 56.

The actuator 58 comprises a rack and pinion gear assembly 84 comprising a rack 86 and pinion gear 88 for lowering and raising the tube 56 inside the gear housing 68. The pinion gear 88 can be made of acetal resin. The rack 86 and pinion gear 88 have matching teeth. As the teeth of the pinion 88 are rotated, they push against the adjacent matching teeth of the rack 86 to raise or lower the attached tube 56, depending on the direction of rotation of the pinion gear 88. An eye bolt 92 has a threaded stem 90 which is attached to the pinion gear 88 for rotating the gear 88. As sufficient torque is applied to a bolt ring 94 of the bolt 92, the bolt 92 and the pinion 88 rotate to lower the rack 86 and the tube 56. A retaining ring 89 is provided on the upper end of the rack 86 to prevent the tube 56 from lowering past a predetermined depth in the reservoir 12.

The tube 56 does not rotate as it is lowered thereby minimizing disturbance of the insulating fluid in the reservoir 12. This is important as the fluid can be highly volatile when it is sufficiently degraded or contaminated. Moreover, because the sampling tool 48 is made mostly of plastic, sparks are not generated when the parts of the tool 48 rub together. This protects against fire and explosion that could be caused by sparks.

The bolt ring 94 protrudes from the gear housing 68 so that the handle 64 can be attached to the ring 94 for remotely rotating the bolt 92. One way that the handle 64 can be made attachable to the ring 94 is by providing a hook on the end of the handle 64. A set screw 96 can be provided to set the tension on the pinion gear 88.

The sampling tool 48 further includes a brass elbow 97 and tube connector 99 for fluidly connecting the upper vertical portion 74 of the tube 56 to a horizontal portion 98 of the tubing 57. The horizontal portion 98 is schematically illustrated in FIG. 3. When the portions 74 and 98 are threadedly attached to the elbow 97, sealing tape should be provided on any threads of the portions 74 and 98 to prevent fluid leakage.

When the sampling tool 48 is lowered into the vault 16, as described above, the adapter 66 fits snugly at the opening 18 of the reservoir 12. The adapter 66 can be made of insulating material to electrically insulate the operator of the tool 48 from the fluid in the reservoir 12. The adapter 66 has an end portion 67 of smaller diameter than the rest of the adapter 66. The end portion 67 can be varied in diameter to fit various sizes of openings 18. The smaller diameter end portion 67 serves as a guide for inserting the sampling tool 48 into the opening 18 of the reservoir 12.

The sampling tool 48 can be made mostly of hard plastic material so it is electrically insulative, light in weight, and resistant to corrosion. The connector housing 70 and the flexible tubing 57 can be made of polyvinyl chloride (PVC). The portions 74 and 76 of the sampling tube 56, the gear housing 68, the adapter 66, the rack 86, and the pinion gear 88 can be made of acetal resin. The eye bolt 92 and the set screw 96 can be made of stainless steel, the retaining ring 89 can be made of hardened carbon steel, and the elbow 97 and connector 99 can be constructed of brass. Alternative materials can be used for all of these parts.

Turning to FIG. 7, a detailed illustration of the connecting assembly 61 and the vacuum-sealing apparatus of the sample bottle 50 and the overflow bottle 52 is provided. These items are conventional in the art. Of particular note is the stop valve 100 which can be alternatively opened or closed to respectively allow or prevent the flow of fluid into the sample bottle 50. The valve 100 can be used to regulate the flow of fluid into the sample bottle 50. The valve 100 is also useful when the sample bottle 50 has been filled to a desired level.

The valve 100 can then be closed just after the pump 54 is turned off to stop the flow of insulating fluid.

As is conventional in the art, the bottles 50 and 52 have stoppers 102 having glass or plastic in-flow tubes 104 and out-flow tubes 106. The tubes 104 and 106 are vacuum-sealed to the connector tubing 62 by clamps 108.

Turning to FIGS. 8 and 9, an alternative to the socket 22 of FIG. 2 is provided by a gripping socket 110. The gripping socket 110 grips the plug 10 without need for tape 31. The plug 10 is gripped by metal balls 112 which partially extend through holes 114. The balls 112 are pushed against the plug 10 by a rubber ring 116. The ring 116 is set into the socket 110 in a groove 118 machined into the gripping socket 110.

The fluid sampling apparatus 46 can also be used to replenish the insulating fluid in the reservoir 12 which has been withdrawn for sampling. The sample bottle 50 is replaced with a similar bottle filled with new insulating fluid. The sampling end 76 is raised above the fluid level in the reservoir 12 and the fluid from the filled bottle is allowed to flow into the reservoir 12. If the fluid flow is too slow, the connector tube 62 to the vacuum pump 54 can be attached to the discharge side of the pump 54 to force the fluid from the filled bottle into the reservoir 12 by air pressure.

Therefore, the apparatus and method of the present invention provide a way to remotely sample insulating fluid in an electrical switch without de-energizing the switch. The removing tool 20 and the apparatus 46 can be operated a distance of at least about 10 feet from the reservoir 12. Moreover, the fluid can be sampled without substantially disturbing the fluid because the thin-walled sampling tube 56 does not rotate when it is inserted into the fluid.

An apparatus and method according to the present invention can be inexpensive and simple to manufacture and use because it has comparatively few parts, is made mostly of plastic, and is manually operable. The apparatus can also be light in weight so it is easily transportable to an electrical switch from which a sample is to be drawn. The apparatus can further be electrically insulative at comparatively high voltages and is resistant to corrosion.

Although the present invention has been described in considerable detail with reference to certain preferred versions thereof, other versions are possible. Therefore, the spirit and scope of the appended claims should not necessarily be limited to the description of the preferred versions contained herein.

What is claimed is:

1. A fluid sampling apparatus for remotely sampling an insulating fluid in an arc-extinguishing reservoir of a high voltage, high amperage electrical switch without de-energizing the switch, the apparatus comprising:
   (a) a sampling tube for withdrawing a sample of the insulating fluid through an opening of the reservoir when a sampling end of the tube is inserted into the reservoir, the sampling tube being made of electrically insulating material having high dielectric strength;
   (b) an actuator attached to the tube for remotely inserting the sampling end into the reservoir and removing the sampling end from the reservoir, a portion of the actuator being remote from the sampling end so that the actuator is operable at a distance of at least about ten feet from the reservoir;
   (c) a support for supporting the sampling tube near the opening of the reservoir, any portion of the support having contact with the opening of the reservoir being made of electrically insulating material having high dielectric strength;
   (d) collection means for fluidly collecting the sample remotely from the sampling end, the tube being in fluid connection between the reservoir and the collection means; and
   (e) connecting means for fluidly connecting the sampling tube remotely from its sampling end to pumping means for pumping the sample from the reservoir through the tube into the collection means.

2. The fluid sampling apparatus of claim 1 wherein the actuator is manually operable.

3. The fluid sampling apparatus of claim 1 wherein the insulating material of the tube and the support is acetal resin.

4. The fluid sampling apparatus of claim 1 wherein the apparatus is light in weight and easily transportable.

5. A fluid sampling apparatus for remotely sampling fluid in a reservoir, the apparatus comprising:
   (a) a sampling tube for withdrawing a sample of the fluid through an opening of the reservoir when a sampling end of the tube is inserted into the reservoir;
   (b) an actuator attached to the tube for remotely inserting the sampling end into the reservoir and removing the sampling end from the reservoir, a portion of the actuator being remote from the sampling end so that the actuator is manually operable at a distance of at least about ten feet laterally from the reservoir;
   (c) a support for supporting the sampling tube near the opening of the reservoir;
   (d) collection means for fluidly collecting the sample remotely from the sampling end, the tube being in fluid connection between the reservoir and the collection means; and
   (e) connecting means for fluidly connecting the sampling tube remotely from its sampling end to pumping means for pumping the sampling from the reservoir through the tube into the collection means.

6. The fluid sampling apparatus of claim 1 or 5 wherein the actuator comprises a rack and pinion gear assembly having the rack affixed to the sampling tube.

7. The fluid sampling apparatus of claim 6 wherein the actuator further comprises an eye bolt attached to the pinion gear of the gear assembly and an elongated handle removably attachable to the bolt for remotely rotating the bolt and the pinion gear to lower the rack and the tube.

8. The fluid sampling apparatus of claim 1 or 5 wherein the support comprises an end adapter fitting onto an opening of the reservoir for installing the apparatus on the reservoir, the adapter having a receiving hole for receiving the sampling tube therethrough.

9. The fluid sampling apparatus of claim 8 wherein the reservoir is in an underground vault and the support further comprises a brace suspended across an opening of the vault and a holding clip attached to the brace for holding the device over the reservoir.

10. The fluid sampling apparatus of claim 1 or 5 further comprising a retainer ring attached to the sampling tube for preventing the tube from lowering beyond a predetermined depth in the reservoir.

11. The fluid sampling apparatus of claim 1 or 5 wherein the actuator inserts and removes the sampling end of the tube into and from the reservoir, respectively, without rotating the tube to minimize disturbance of the fluid.

12. The fluid sampling apparatus of claim 1 or claim 5 wherein the pumping means comprises a vacuum pump.

13. The fluid sampling apparatus of claim 12 wherein the collection means comprises a sample bottle in fluid connection between the sampling tube and the vacuum pump.

14. The fluid sampling apparatus of claim 1 or claim 5 further comprising a stop valve for opening and closing a fluid connection between the sampling tube and the collection means.

15. The fluid sampling apparatus of claim 5 wherein the support comprises an outer tube containing the sampling tube therein, the outer tube forming an outer cavity between the outer tube and the sampling tube, the apparatus further comprising means for sucking the fluid through the sampling tube.

16. The fluid sampling apparatus of claim 5 wherein the collection means comprises a sampling means for collecting a sample of the fluid and an overflow collector means for collecting excess fluid from the sampling means.

17. The fluid sampling apparatus of claim 5 wherein the apparatus is light in weight and easily transportable.

18. A fluid sampling apparatus for remotely sampling an insulating fluid in an arc-extinguishing reservoir of a high voltage, high amperage electrical switch inside an underground vault without de-energizing the switch, the apparatus comprising:
 (a) a sampling tube for withdrawing a sample of the fluid through an opening of the reservoir when a sampling end of the tube is inserted into the reservoir;
 (b) a rack and pinion gear assembly having the rack affixed to the tube for inserting the sampling end into the reservoir and removing the sampling end from the reservoir wherein the gear assembly lowers and raises the tube without rotating the tube to minimize disturbance of the fluid;
 (c) a supporting structure having a gear housing proximate an upper vertical portion of the tube, an end adapter proximate the sampling end, and a connector housing attached to and between the end adapter and the gear housing; the gear housing, adapter, and the connector housing having receiving holes for receiving the sampling tube therethrough; the gear housing surrounding at least a portion of the gear assembly; the adapter fitting onto the opening of the reservoir for installing the sampling apparatus on the opening; the supporting structure further having a brace suspended across an opening of the underground vault, and a clip attached to the brace for supporting the tube in the vault;
 (d) an eye bolt attached to the pinion gear, the eye bolt and the pinion gear rotating to raise and lower the rack and the tube, the eye bolt having a bolt ring extending from the gear housing;
 (e) an elongated handle attachable to the bolt ring for manually and remotely rotating the eye bolt to lower and raise the sampling tube, a portion of the handle being remote from the sampling end of the tube so that the handle is operable at least a distance of about ten feet from the reservoir;
 (f) a vacuum-sealed sampling collector bottle;
 (g) a vacuum-sealed overflow bottle, the collector bottle being in fluid connection between the sampling tube and the overflow bottle; and
 (h) a vacuum pump in fluid connection with the overflow bottle downstream from the overflow bottle for remotely pumping the fluid sample from the reservoir, through the sampling tube, and into the sampling bottle when the tube is inserted into the reservoir by the gear assembly; wherein the sampling tube and the end adapter are made of an electrically insulating material of high dielectric strength.

19. The fluid sampling apparatus of claim 18 wherein the apparatus is light in weight and easily transportable.

20. A method for remotely sampling insulating fluid from an arc-extinguishing reservoir of a high voltage, high amperage electrical switch while the switch remains energized, comprising the steps of:
 (a) remotely removing a plug from an opening of the reservoir with a remotely operable removing tool, an operator of the removing tool being no less than about ten feet from the switch while removing the plug;
 (b) placing a fluid sampling tool on the opening;
 (c) remotely inserting a sampling tube of the sampling tool into the reservoir, an operator of the sampling tool being no less than about ten feet from the switch while lowering the tube;
 (d) pumping a sample of the insulating fluid from the reservoir through the tube into a sampling collector;
 (e) remotely removing the tube from the reservoir;
 (f) removing the sampling tool from the switch; and
 (g) remotely replacing the plug on the opening of the switch.

21. The method of claim 20 wherein the step of pumping is performed with a vacuum pump.

22. The method of claim 20 wherein the steps of inserting and removing the tube are performed without rotating the tube to minimize disturbance of the fluid.

23. A fluid sampling kit for remotely sampling an insulating fluid in an arc-extinguishing reservoir of a high voltage, high amperage electrical switch without de-energizing the switch, comprising:
 (a) a removing tool for remotely removing a plug from an opening of the reservoir, the tool being remotely operable from a distance of at least about ten feet from the reservoir; and
 (b) a fluid sampling apparatus comprising:
  (i) a sampling tube for sucking a sample of the fluid through the opening of the reservoir when a sampling end of the tube is inserted into the reservoir, the sampling tube being made of electrically insulating material having high dielectric strength;
  (ii) an actuator attached to the tube for remotely inserting the sampling end into the reservoir and removing the sampling end from the reservoir, a portion of the actuator being remote from the sampling end so that the actuator is operable from a distance of at least about ten feet form the reservoir;
  (iii) a support for supporting the sampling tube near the opening of the reservoir, a portion of the support having contact with the opening of the reservoir and being made of electrically insulating material having high dielectric strength;

(iv) collection means for collecting the sample, the sampling tube being in fluid connection between the reservoir and the collection means; and (v) pumping means in fluid connection with the collection means for pumping the fluid sample from the reservoir through the tube into the collection means when the tube is inserted into the reservoir.

24. The kit of claim 23 wherein the removing tube comprises (1) a socket fitting the plug, the socket having retaining means therein for retaining the plug in the socket when the plug is removed from the opening, (2) a socket extender for rotating the socket, the socket extender having a socket end and a handle end and being removably attachable at its socket end to the socket, (3) a ratchet wrench removably attachable at its first end to the handle end of the extender, the wrench extending at a substantially right angle from the extender and ratcheting in one direction of rotation of the wrench about an axis extending through the extender, and (4) a plurality of pull cords, attached to and extending from a second end of the wrench, for rotating the wrench in opposite directions of rotation about the axis.

25. The kit of claim 24 wherein the retaining means comprises sticky tape attached to the back wall of the socket.

26. The kit of claim 24 wherein the retaining means comprises a combination of balls and a rubber ring whereby the balls are pushed against the plug by the ring set in a groove on an outer surface of the socket.

27. The kit of claim 23 wherein the insulating material of the tube and the support is acetal resin.

28. The kit of claim 23 wherein the actuator comprises a rack and pinion gear assembly having the rack affixed to the tube.

29. The kit of claim 28 wherein the pinion gear is attached to an eye bolt, the bolt being attachable to an elongated handle for rotating the bolt and pinion gear to lower the rack and the tube.

30. The kit of claim 23 wherein the collection means comprises a sample bottle and an overflow bottle, the sample bottle being in fluid connection between the tube and the overflow bottle.

31. The kit of claim 23 wherein the actuator lowers and raises the sampling tube without rotating the tube to minimize disturbance of the fluid.

32. The fluid sampling kit of claim 23 wherein the kit is light in weight and easily transportable.

33. A fluid sampling apparatus for remotely sampling fluid in a reservoir, the apparatus comprising:
(a) a sampling tube for withdrawing a sample of the fluid through an opening of the reservoir when a sampling end of the tube is inserted into the reservoir;
(b) an actuator attached to the tube for remotely inserting the sampling end into the reservoir and removing the sampling end from the reservoir, a portion of the actuator being remote from the sampling end so that the actuator is operable at a distance of at least about 10 feet from the reservoir, the actuator comprising,
  (i) a rack and pinion gear assembly having the rack affixed to the sampling tube;
  (ii) an eyebolt attached to the pinion gear of the gear assembly; and
  (iii) an elongated handle removably attachable to the bolt for remotely rotating the bolt and the pinion gear to lower the rack and the tube;
(c) a support for supporting the sampling tube near the opening of the reservoir;
(d) collection means for fluidly collecting the sample remotely from the sampling end, the tube being in fluid connection between the reservoir and the collection means; and
(e) connecting means for fluidly connecting the sampling tube remotely from its sampling end to pumping means for pumping the sample from the reservoir through the tube into the connection means.

* * * * *